(12) United States Patent
Bansal et al.

(10) Patent No.: US 11,565,080 B2
(45) Date of Patent: Jan. 31, 2023

(54) CATHETER TIP ASSEMBLY FOR A CATHETER SHAFT

(71) Applicant: St. Jude Medical, Cardiology Division, Inc., St. Paul, MN (US)

(72) Inventors: Varun Bansal, Maple Grove, MN (US); Jodee M. Wakefield, Minneapolis, MN (US); Brent Ford, Minneapolis, MN (US); Ryan D. Hendrickson, Albertville, MN (US); David J. Kim, Plymouth, MN (US); Zachary L. Helgeson, Richfield, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 332 days.

(21) Appl. No.: 16/782,382

(22) Filed: Feb. 5, 2020

(65) Prior Publication Data
US 2020/0254216 A1    Aug. 13, 2020

Related U.S. Application Data

(60) Provisional application No. 62/803,856, filed on Feb. 11, 2019.

(51) Int. Cl.
*A61M 25/01* (2006.01)
*A61M 25/00* (2006.01)

(52) U.S. Cl.
CPC .... *A61M 25/0068* (2013.01); *A61M 25/0136* (2013.01); *A61M 2025/0163* (2013.01)

(58) Field of Classification Search
CPC ................ A61M 25/0068; A61M 25/0069
See application file for complete search history.

(56) References Cited

U.S. PATENT DOCUMENTS 3,589,368 A * 6/1971 Jackson ............ A61M 25/0068
604/246
5,192,290 A   3/1993 Hilal
(Continued)

FOREIGN PATENT DOCUMENTS

EP    2452719 A1   5/2012
EP    2712647 A1   4/2014
(Continued)

OTHER PUBLICATIONS

Translation of JP H08112352 A (Year: 1994).*
(Continued)

*Primary Examiner* — Laura A Bouchelle
(74) *Attorney, Agent, or Firm* — Armstrong Teasdale LLP

(57) ABSTRACT

Disclosed herein is a catheter tip sized and configured to fit onto a distal end of a catheter shaft, the catheter shaft having a shaft outer diameter. The catheter tip includes a base, a tip having an arcuate shape, an outer surface extending from the base to the tip along a longitudinal axis, the outer surface having a diameter at the base that is substantially equal to the shaft outer diameter, and an inner surface extending from the base, wherein the inner surface defines a first region having a first diameter and a second region having a second diameter, wherein the second diameter is less than the first diameter, and wherein the second region is distal of the first region and configured to receive at least one component extending beyond the distal end of the catheter shaft.

10 Claims, 10 Drawing Sheets

(56) References Cited

U.S. PATENT DOCUMENTS

| | | | |
|---|---|---|---|
| 5,451,216 A * | 9/1995 | Quinn | A61M 1/84 604/270 |
| 5,823,955 A | 10/1998 | Kuck et al. | |
| 6,511,474 B1 * | 1/2003 | Andersen | A61J 15/0026 604/270 |
| 8,048,058 B2 * | 11/2011 | Fulford | A61M 25/001 604/523 |
| 2001/0027309 A1 | 10/2001 | Elsberry | |
| 2002/0169457 A1 | 11/2002 | Quinn | |
| 2007/0270791 A1 | 11/2007 | Wang et al. | |
| 2009/0264980 A1 | 10/2009 | Mackay | |
| 2011/0224625 A1 * | 9/2011 | Flickinger | A61M 25/0105 604/257 |
| 2014/0276916 A1 | 9/2014 | Ahluwalia et al. | |
| 2018/0093069 A1 | 4/2018 | Bressler et al. | |

FOREIGN PATENT DOCUMENTS

| | | | | |
|---|---|---|---|---|
| JP | 08112352 A * | 5/1996 | | |
| JP | 5348675 B1 | 11/2013 | | |
| WO | 9107200 A1 | 5/1991 | | |
| WO | WO-9533509 A1 * | 12/1995 | | A61M 25/0069 |

OTHER PUBLICATIONS

Extended European Search Report for EP Patent Application No. 20155851, dated Jun. 22, 2020, 10 pages.
Communication pursuant to Article 94(3) EPC for EP Patent Application No. 20155851, dated Jul. 4, 2021, 5 pages.

* cited by examiner

CATHETER TIP ASSEMBLY FOR A CATHETER SHAFT

CROSS REFERENCE TO RELATED APPLICATIONS

This application claims priority to provisional application Ser. No. 62/803,856, filed Feb. 11, 2019, which is incorporated herein in its entirety.

FIELD OF THE DISCLOSURE

The present disclosure relates generally to medical devices that are used in the human body. In particular, in many aspects, the present disclosure relates to a catheter tip assembly sized and configured for placement on the distal end of a catheter shaft in order to improve the overall performance of the catheter shaft during a medical procedure.

BACKGROUND

The human heart muscle routinely experiences electrical currents traversing its many surfaces and ventricles, including the endocardial surfaces. Just prior to each heart contraction, the heart muscle is said to "depolarize" and "repolarize," as electrical currents spread across the heart and throughout the body. In a healthy heart, the surfaces and ventricles of the heart will experience an orderly progression of a depolarization wave. In an unhealthy heart, such as those experiencing atrial arrhythmia, including for example, ectopic atrial tachycardia, atrial fibrillation, and atrial flutter, the progression of the depolarization wave may not be so orderly. Arrhythmias may persist as a result of scar tissue or other obstacles to rapid and uniform depolarization. These obstacles may cause depolarization waves to repeat a circuit around some part of the heart. Atrial arrhythmia can create a variety of dangerous conditions, including irregular heart rates, loss of synchronous atrioventricular contractions, and stasis of blood flow, all of which can lead to a variety of ailments and even death.

Medical devices, such as, for example, mapping, electroporation, and/or electrophysiology catheters, are used in a variety of diagnostic and/or therapeutic medical procedures to treat such heart arrhythmias. Typically in a procedure, a catheter is manipulated through a patient's vasculature to a patient's heart, for example, and carries one or more electrodes that may be used for mapping, ablation, diagnosis, and/or to perform other functions. Once at an intended site, treatment may include radio frequency (RF) ablation, cryoablation, lasers, chemicals, high-intensity focused ultrasound, etc. As is readily apparent, such treatment requires precise control of the catheter during manipulation to, from, and at a mapping and/or treatment site, which can invariably be a function of a user's skill level. Because insertion of the catheter is typically done in the femoral artery, the catheter must traverse a distance before reaching the heart. As such, the catheter must travel freely while preventing any possible surfaces of the catheter from catching or snagging on the interior surface of the blood vessels or other tissue.

BRIEF SUMMARY OF THE DISCLOSURE

In one embodiment, the present disclosure is directed to a catheter tip sized and configured to fit onto a distal end of a catheter shaft, the catheter shaft having a shaft outer diameter. The catheter tip includes a base, a tip having an arcuate shape, an outer surface extending from the base to the tip along a longitudinal axis, the outer surface having a diameter at the base that is substantially equal to the shaft outer diameter, and an inner surface extending from the base, wherein the inner surface defines a first region having a first diameter and a second region having a second diameter, wherein the second diameter is less than the first diameter, and wherein the second region is distal of the first region and configured to receive at least one component extending beyond the distal end of the catheter shaft.

In another embodiment, the present disclosure is directed to a catheter assembly. The catheter assembly includes a catheter handle, a catheter shaft having a shaft outer diameter, a proximal end, and a distal end, and a catheter tip coupled to the distal end of the catheter shaft. The catheter tip includes a base, a tip having an arcuate shape, an outer surface extending from the base to the tip along a longitudinal axis, the outer surface having a diameter at the base that is substantially equal to the shaft outer diameter, and an inner surface extending from the base, wherein the inner surface defines a first region having a first diameter and a second region having a second diameter, wherein the second diameter is less than the first diameter, and wherein the second region is distal of the first region and configured to receive at least one component extending beyond the distal end of the catheter shaft.

In yet another embodiment, the present disclosure is directed to a catheter tip sized and configured to fit onto a distal end of a catheter shaft, the catheter shaft having a shaft outer diameter. The catheter tip includes a base, a tip having an arcuate shape, an outer surface extending from the base to the tip along a longitudinal axis, and an inner surface extending from the base, wherein the inner surface defines at least one region within the catheter tip.

The foregoing and other aspects, features, details, utilities and advantages of the present disclosure will be apparent from reading the following description and claims, and from reviewing the accompanying drawings.

DETAILED DESCRIPTION OF THE DISCLOSURE

Figure 1:
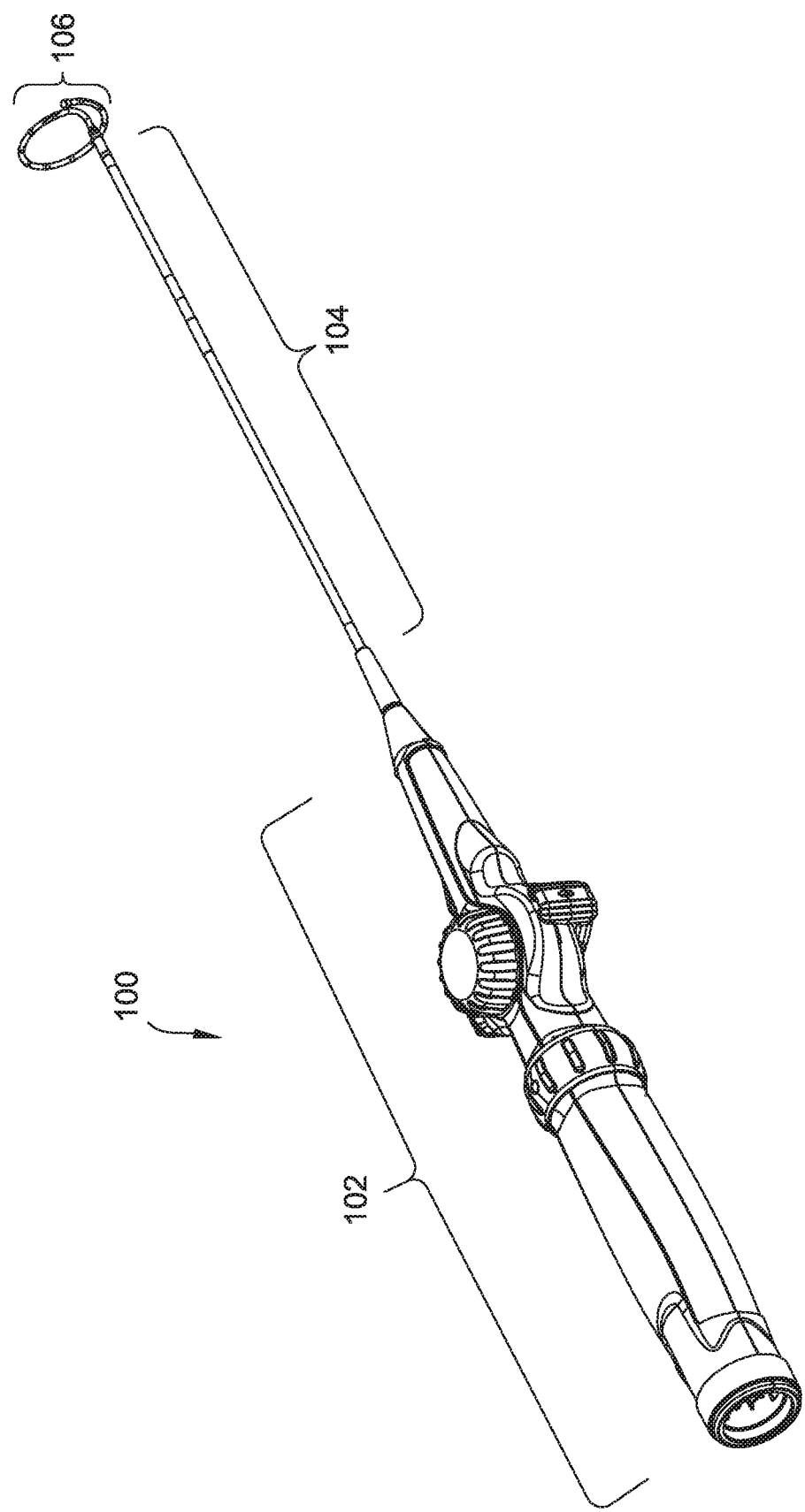
FIG. 1 is an isometric view of one embodiment of a catheter assembly including a catheter handle and steering actuator for deflecting a catheter shaft.

The present disclosure provides a catheter tip assembly suitable for direct attachment and use on the distal end of a catheter shaft, such as a catheter shaft including a loop on the distal end. During the manufacturing process for some catheters, one or more components such as nitinol wires and/or Inconel sleeves of the catheter that feed through a lumen of the catheter may extend past the distal end of the catheter shaft; that is, one or more of these components may extend outward of the catheter shaft to form a small protrusion. Even if these components are generally machined to be rounded in nature and only extend past the distal end of the catheter shaft by only millimeters (or less), these components may potentially in some embodiments contact the vasculature or the anatomy of a patient during use (e.g., during insertion or removal). The catheter tips of the present disclosure are sized and configured for attachment to the distal end of a catheter shaft to cover such components, allowing the shaft to be easily inserted into the introducer during use and to move more easily inside the patient's anatomy.

In many embodiments, disclosed herein is a catheter tip configured to fit snugly onto the outer diameter of the distal end of a catheter shaft, which may be in some embodiments, constructed of a thermoplastic polymer such as a Pellethane® thermoplastic polymer. The catheter tip generally includes a tip outer surface and a tip inner surface. The tip outer surface includes a rounded and symmetric shape having a tip outer diameter that is larger than the shaft outer diameter, and the tip outer surface diameter tapers down to substantially the same diameter as the shaft outer diameter thereby creating a smooth (i.e., generally substantially free of perceptible protrusions, lumps or indentations), continuous profile when the catheter tip is placed on the distal end of the catheter shaft. The tip inner surface may include a first step region having a first step inner diameter substantially the same as the shaft outer diameter and is configured to receive the distal end of the catheter shaft, and a second step region having a second step inner diameter smaller than the first step inner diameter and is continuously connected to the first step region.

Because the catheter tips of the present disclosure are designed to fit onto the distal end of the catheter shaft, the diameter of the outer surface of the catheter shaft is substantially the same as the diameter of the inner surface of the catheter tips. In this context, "substantially the same" means that they two components fit together snugly but without difficulty or significant gaps therebetween. There is substantially zero tolerance and substantially no gap between these components. When a biocompatible adhesive is used to fix the catheter tip to the distal end of the catheter shaft, the adhesive forms a film between the two surfaces such that there is substantially no gap between them. In some aspects, the adhesive is also applied to the outer surfaces of the distal end of the catheter shaft and the catheter tip such that it covers the junction between the two components.

In some embodiments of the present disclosure, the distal end of the catheter shaft terminates in a loop configuration. Generally, the loop is a circular loop, an oval loop, or like shape, located on the distal end of the catheter shaft as part of the distal loop subassembly. The loop may be of a fixed or variable size. In some aspects, the loop is a fixed size. In some aspects, the loop is a variable size.

In embodiments, the catheter including the catheter tip as described herein is a unidirectional catheter meaning the tip is able to deflect only along a single plane. In other embodiments, the catheter is a bidirectional catheter meaning the tip is able to deflect along at least two different planes. For example, for a bidirectional catheter, the tip may deflect in a first direction along a first plane and in a second direction in a second plane that is orthogonal to the first plane.

The distal end of the catheter shaft and the catheter tip may or may not be fabricated from the same material. In some embodiments, the catheter tip may be formed from a single material while in other embodiments it may be formed from two or more materials. Attachment of the catheter tip to the catheter shaft is completed in a manner such that the catheter tip is secured in such a manner that it is substantially stable during use. In some embodiments, attachment is done using a biocompatible adhesive. The adhesive is placed on at least one of the two surfaces to be adhered together. For example, the outer surface of the distal end of the catheter shaft will be in direct contact with the inner surface of the catheter tip. As such, the adhesive is placed on one or both surfaces before the distal end of the catheter shaft is placed inside of the lumen of the catheter tip. The biocompatible adhesive is allowed to cure and/or dry for a predetermined period of time to ensure that the catheter tip is securely fastened onto the distal end of the catheter shaft. In some embodiments, ultraviolet curable biocompatible adhesives may be particularly suitable.

The catheter tips of the present disclosure as described herein may be fabricated from any suitable biocompatible polymeric or other material. In some embodiments, thermoplastic polymers are suitable construction materials. In other embodiments, the catheter tip is made from a polymer selected from the group consisting of ABS, acetal, PEEK, polyurethane, polypropylene, and combinations thereof. In other embodiments, suitable materials for construction may include polycarbonate materials, including clear polycarbonate materials.

The thickness of the tip varies based on the design of the tip. In some embodiments, the thickness of the tip is from about 0.001 inches to about 0.030 inches. In some other embodiments, the thickness of the tip is from about 0.002 to about 0.015 inches. In this context about means±10%.

Referring now to the figures, FIG. 1 is a generalized illustration of one possible catheter assembly 100 suitable for use with the catheter tips disclosed and described herein. Catheter assembly 100 includes a catheter handle 102 and a catheter shaft 104. In some aspects, the distal end of catheter shaft 104 includes a distal loop subassembly 106 that is part of catheter shaft 104. Various aspects of the distal loop subassembly are illustrated elsewhere herein, for example, FIGS. 4 and 5. In some aspects, the catheter tip is installed on the distal end of the distal loop subassembly 106. Catheter assembly 100 may be used for mapping anatomic structures, as described herein. However, those of skill in the art will appreciate that the systems and methods described herein may also be implemented in other types of catheters (e.g., catheters used for ablation and/or electroporation).

Figure 2:
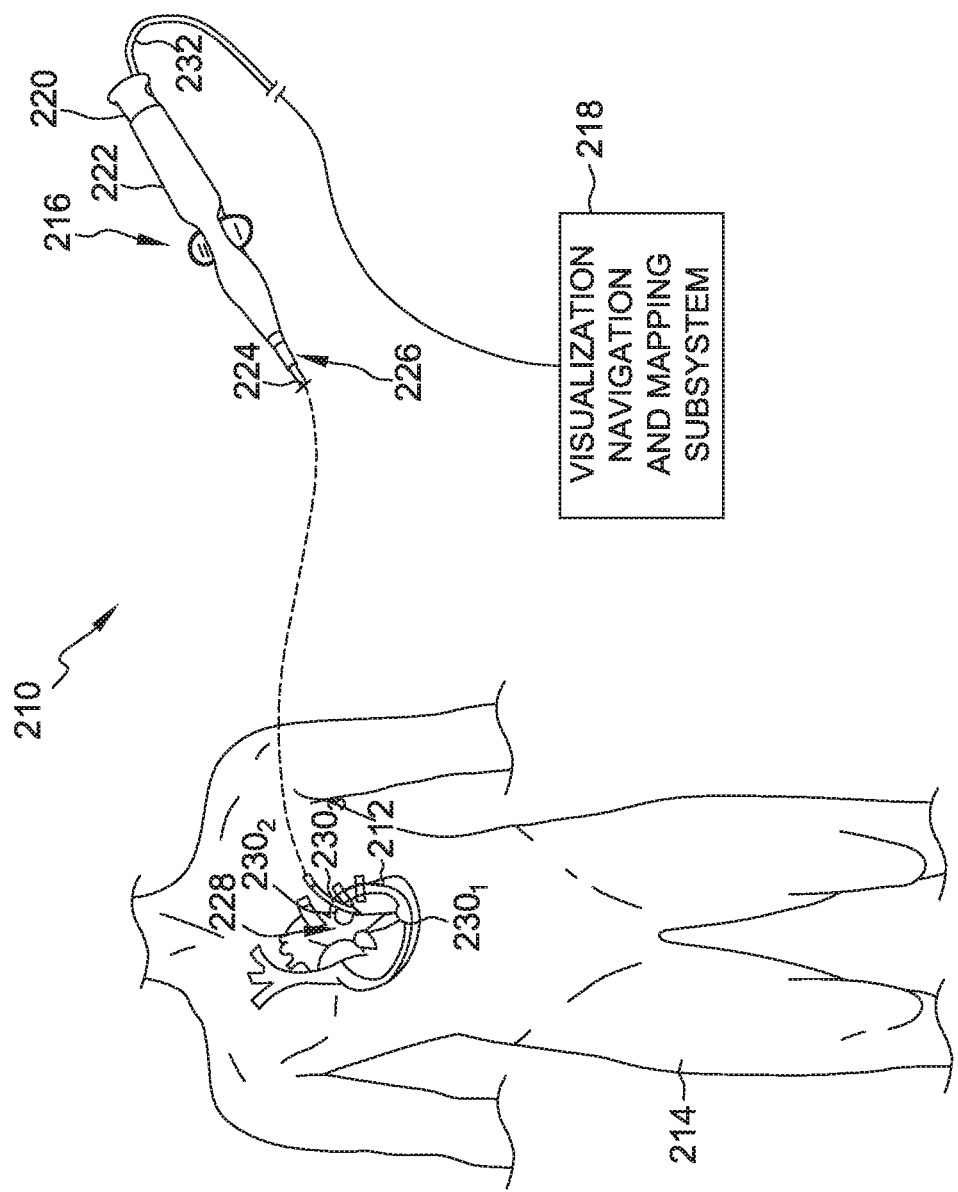
FIG. 2 is a schematic diagram of one embodiment of a system for performing one or more diagnostic and/or therapeutic functions that may use the catheter assembly shown in FIG. 1.

FIG. 2 illustrates one exemplary embodiment of a system 210 for performing one or more diagnostic and/or therapeutic functions on or for a tissue 212 of a body 214. System 210 may use, for example, catheter assembly 100 (shown in FIG. 1). In an exemplary embodiment, tissue 212 includes heart or cardiac tissue within a human body 214. It should be understood, however, that system 210 may find application in connection with a variety of other tissues within human and non-human bodies, and therefore, the present disclosure is not meant to be limited to the use of system 210 in connection with only cardiac tissue and/or human bodies.

System 210 may include a medical device (e.g., a catheter 216) and a subsystem 218 for the visualization, navigation, and/or mapping of internal body structures (hereinafter referred to as the "visualization, navigation, and mapping subsystem 218", "subsystem 218", or "mapping system").

In this embodiment, medical device includes a catheter 216, such as, for example, an electrophysiology catheter. In other exemplary embodiments, medical device may take a form other than catheter 216, such as, for example and without limitation, a sheath or catheter-introducer, or a catheter other than an electrophysiology catheter. For clarity and illustrative purposes only, the description below will be limited to embodiments of system 210 wherein medical device is a catheter (catheter 216).

Catheter 216 is provided for examination, diagnosis, and/or treatment of internal body tissues such as tissue 212. Catheter 216 may include a cable connector 220 or interface, a handle 222, a shaft 224 having a proximal end 226 and a distal end 228 (as used herein, "proximal" refers to a direction toward the end of catheter 216 near handle 222, and "distal" refers to a direction away from handle 222), and one or more sensors, such as, for example and without limitation, a plurality of electrodes 230 (i.e., $230_1$, $230_2, \ldots, 230_N$), mounted in or on shaft 224 of catheter 216 at or near distal end 228 of shaft 224. Distal end 228 of catheter 216 may include a distal loop subassembly, such as distal loop subassembly 106 (shown in FIG. 1).

In other embodiments, catheter 216 may further include other conventional components such as, for example and without limitation, steering wires and actuators, irrigation lumens and ports, pressure sensors, contact sensors, temperature sensors, additional electrodes and corresponding conductors or leads, and/or ablation elements (e.g., ablation electrodes, high intensity focused ultrasound ablation elements, and the like).

Connector 220 provides mechanical and electrical connection(s) for one or more cables 232 extending, for example, from visualization, navigation, and mapping subsystem 218 to one or more sensors mounted on catheter 216. In other embodiments, connector 220 may also provide mechanical, electrical, and/or fluid connections for cables extending from other components in system 210, such as, for example, an ablation system and a fluid source (when catheter 216 includes an irrigated catheter). Connector 220 is disposed at proximal end 226 of catheter 216.

Handle 222 provides a location for a user to hold catheter 216 and may further provide means for steering or guiding shaft 224 within body 214. For example, handle 222 may include means to manipulate one or more steering wires extending through catheter 216 to distal end 228 of shaft 224 to steer shaft 224. It will be appreciated by those of skill in the art that the construction of handle 222 may vary. In other embodiments, the control of catheter 216 may be automated such as by being robotically driven or controlled, or driven and controlled by a magnetic-based guidance system. Accordingly, catheters controlled either manually or automatically are both within the spirit and scope of the present disclosure.

Shaft 224 is an elongate, tubular, and flexible member configured for movement within body 214. Shaft 224 supports, for example and without limitation, electrodes 230, associated conductors, and possibly additional electronics used for signal processing or conditioning. Shaft 224 may also permit transport, delivery and/or removal of fluids (including irrigation fluids, cryogenic ablation fluids, and body fluids), medicines, and/or surgical tools or instruments. Shaft 224, which may be made from conventional materials such as polyurethane, defines one or more lumens configured to house and/or transport electrical conductors, fluids, or surgical tools. Shaft 224 may be introduced into a blood vessel or other structure within body 214 through a conventional introducer. Shaft 224 may then be steered or guided through body 214 to a desired location such as tissue 212. Distal end 228 of shaft 224 may be the main portion of catheter 216 that contains electrodes 230 or other sensors for acquiring positioning data.

Visualization, navigation, and mapping subsystem 218 may be used to determine the positions of electrodes 230 or other sensors. These positions may be projected onto a geometrical anatomical model. In some embodiments, visualization, navigation, and mapping subsystem 218 includes a magnetic field-based system. For example visualization, navigation, and mapping subsystem 218 may include an electrical field- and magnetic field-based system such as the ENSITE PRECISION™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 228 may include at least one magnetic field sensor—e.g., magnetic coils (not shown). If two or more magnetic field sensors are utilized, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In other exemplary embodiments, subsystem 218 may utilize systems other than electric field-based systems. For example, subsystem 218 may include a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, subsystem 218 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No. 7,386,339 entitled "Medical Imaging and Navigation System," the disclosures of which are incorporated herein by reference in their entireties.

In a further exemplary embodiment, subsystem 218 may utilize a combination electric field-based and magnetic field-based system as generally shown with reference to U.S. Pat.

No. 7,536,218 entitled "Hybrid Magnetic-Based and Impedance Based Position Sensing," the disclosure of which is incorporated herein by reference in its entirety. In yet still other exemplary embodiments, the subsystem 218 may comprise or be used in conjunction with other commonly available systems, such as, for example and without limitation, fluoroscopic, computed tomography (CT), and magnetic resonance imaging (MRI)-based systems.

Although not shown in FIG. 2, in some embodiments, system 210 may include suitable components to perform electroporation and/or ablation (e.g., RF ablation). It should be understood that in such embodiments, variations are possible as to the type of ablation energy provided (e.g., cryoablation, ultrasound, etc.).

Referring back to FIG. 1, catheter assembly 100 includes distal loop subassembly 106 at the distal end. A diameter of distal loop subassembly 106 may be variable in some embodiments. Alternatively, in other embodiments of the present disclosure, the diameter of distal loop subassembly 106 may be fixed.

In at least some embodiments where the diameter is variable, catheter assembly 100 includes a loop member adjustment assembly or mechanism for allowing an operator to adjust the diameter of distal loop subassembly 106; that is, an assembly or mechanism to increase or decrease the diameter of distal loop subassembly 106. This diameter adjustment of distal loop subassembly 106 may be done at any time during a procedure, and may further be done with or without deflection of the distal end of catheter assembly 100; that is, any deflection of the distal end is independent of any diameter adjustment of distal loop subassembly 106 in accordance with the present disclosure. This independent adjustment may be achieved through the use of multiple pull wires contained within catheter assembly 100, for example, as described in U.S. Pat. App. Pub. No. 2017/0291008 entitled "Mapping Variable Loop Catheter Handle", the disclosure of which is incorporated herein by reference in its entirety. By having the capability to adjust the diameter of distal loop subassembly 106 before or during a procedure, an operator may be able to more effectively navigate the vasculature of a patient as described herein and improve patient outcomes as noted above.

Figure 3:
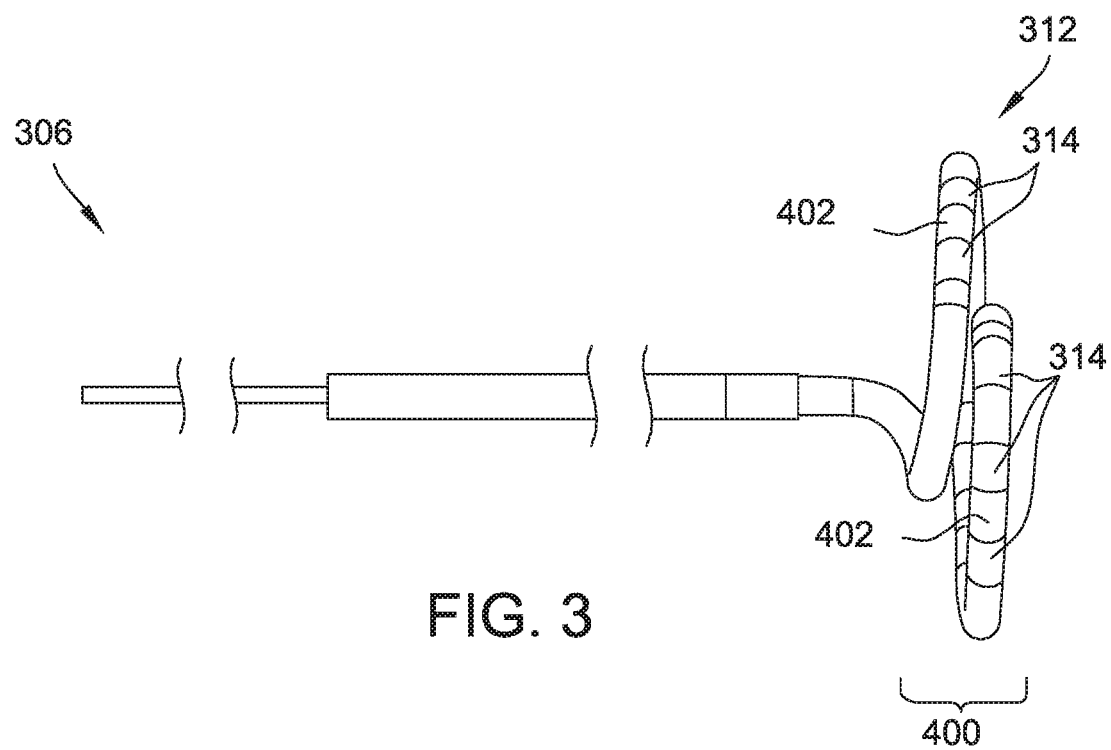
FIG. 3 is a side view of a distal loop subassembly that may be used with the catheter assembly shown in FIG. 1.
Figure 4:
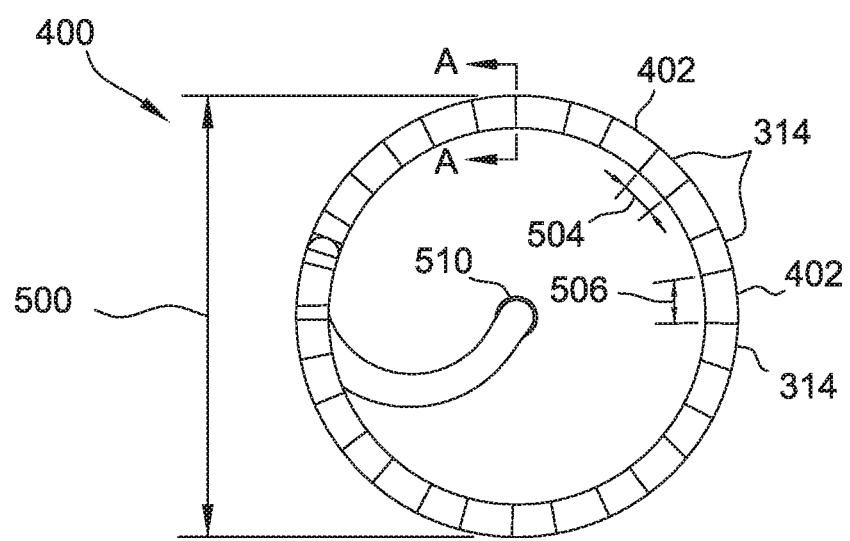
FIG. 4 is an end view of the distal loop subassembly of FIG. 3.

FIGS. 3 and 4 illustrate a distal loop subassembly 306 that may be used, in some embodiments, with catheter 216 (shown in FIG. 2) and/or catheter assembly 100 (shown in FIG. 1). Specifically, FIG. 3 is a side view of distal loop subassembly 306 with a variable diameter loop 400 at distal end 312. FIG. 4 is and end view of variable diameter loop 400 of distal loop subassembly 306.

As shown in FIGS. 3 and 4, a plurality of catheter electrodes 314 mounted on distal loop subassembly 306 may be used for a variety of diagnostic and therapeutic purposes including, for example and without limitation, cardiac mapping and/or ablation. For example, one or more of catheter electrodes 314 may perform a location or position sensing function. More particularly, one or more of catheter electrodes 314 may be configured to be a positioning sensor(s) that provides information relating to the location (position and orientation) of distal loop subassembly 306.

Variable diameter loop 400 is located at a distal end of a catheter shaft 510 and has a diameter 500 transitionable between an expanded (also referred to as "open") diameter (shown in FIG. 4) and a retracted (also referred to as "closed") diameter (not shown). In the example embodiment, the expanded diameter is approximately twenty seven mm and the retracted diameter is approximately fifteen mm. In other embodiments, diameter 500 may be variable between any suitable open and closed diameters.

In this embodiment, variable diameter loop 400 includes fourteen catheter electrodes 314 evenly spaced around the circumference of variable diameter loop 400. In other embodiments, variable diameter loop 400 may include any suitable number of catheter electrodes 314 made of any suitable material. Each catheter electrode 314 is separated from each other catheter electrode by an insulated gap 402. In the example embodiment, each catheter electrode 314 has a same length 504 (shown in FIG. 4) and each insulated gap 402 has a same length 506 as each other gap 402. Length 504 and length 506 are both about 2.5 mm in the example embodiment. In other embodiments, length 504 and length 506 may be different from each other. Moreover, in some embodiments, catheter electrodes 314 may not all have the same length 504 and/or insulated gaps 402 may not all have the same length 506. In some embodiments, catheter electrodes 314 are not spaced evenly around the circumference of variable diameter loop 400.

As explained above, in many embodiments, a catheter tip is installed on the distal end of the distal loop subassembly 106. The catheter tips described herein are sized and configured to allow the catheter to be easily inserted into an introducer during use and to move more easily inside the patient's anatomy.

Figure 5C:
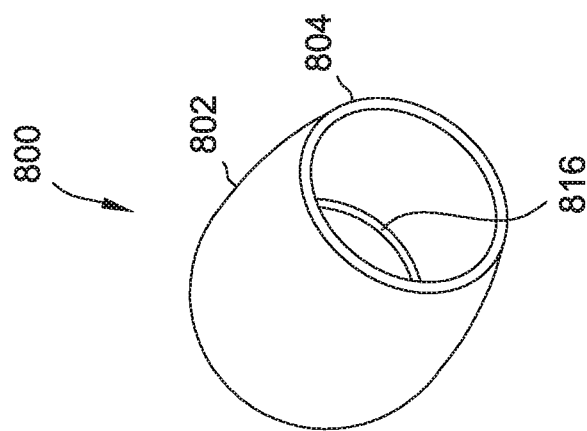
FIGS. 5A-5C illustrate one embodiment of a stepped catheter tip in accordance with the present disclosure.
Figure 5B:
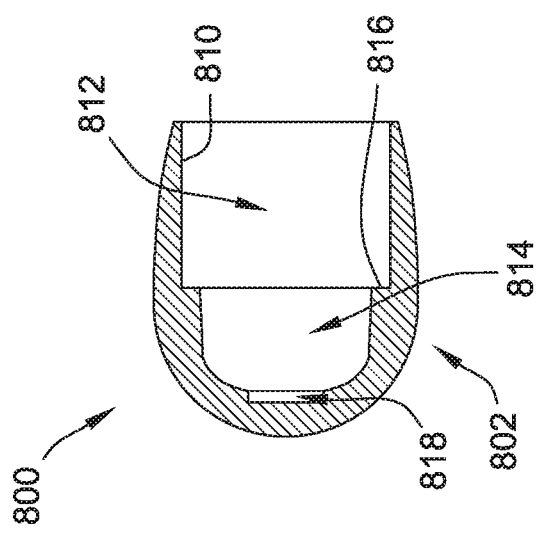
Figure 5A:
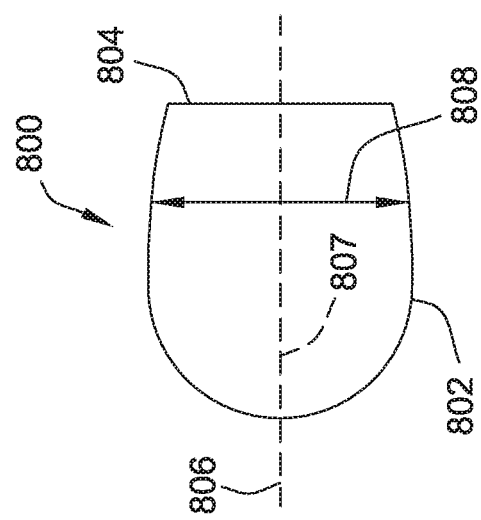

For example, FIGS. 5A-5C show one embodiment of a catheter tip 800. Specifically, FIG. 5A is a side view of catheter tip 800, FIG. 5B is a side cross-sectional view of catheter tip 800, and FIG. 5C is a perspective view of catheter tip 800. As shown in FIGS. 5A-5C, an outer surface 802 of catheter tip 800 has a generally rounded and symmetric design.

Catheter tip 800 extends from a base 804 to a tip 806 along a longitudinal axis 807. Tip 806 has an arcuate, atraumatic shape. The arcuate atraumatic shape of tip 806 allows the end of catheter shaft 510 to be easily introduced into an introducer of the catheter and move easily inside the anatomy of a patient without causing tissue damage.

Outer surface 802 of catheter tip 800 defines an outer diameter 808 of catheter tip 800. As shown in FIG. 5C, a cross-sectional profile of catheter tip 800 is generally circular (i.e., when viewing catheter tip 800 along longitudinal axis 807). In some embodiments, the cross-sectional profile of catheter tip 800 has an oval shape. At base 804, outer diameter 808 tapers to form a substantially smooth transition with a distal end of catheter shaft 510 (not shown in FIGS. 5A and 5B).

As shown in FIG. 5B, catheter tip 800 includes an inner surface 810 that has a stepped arrangement. Specifically, inner surface 810 defines a first region 812 that fits over the distal end of catheter shaft 510. In some embodiments, a biocompatible adhesive is applied on inner surface 810 in first region 812 to ensure that catheter tip 800 does not separate from catheter shaft 510. Inner surface 810 further defines a second region 814 that has a smaller diameter than first region 812. Specifically, inner surface 810 includes a lip 816 that is oriented perpendicular to longitudinal axis 807 and that is located between first and second regions 812 and 814. In operation, the distal end of catheter shaft 510 contacts lip 816 to prevent the distal end of catheter shaft 510 entering second region 814.

Second region 814 is configured to accommodate any wires or other components of the catheter that extend past the distal end of catheter shaft 510 (see, e.g., FIGS. 13A-13E). In some embodiments, wire or other components of catheter that extend into second region 814 are bonded to inner surface 810 in second region (e.g., using a biocompatible adhesive). As shown in FIG. 5B, inner surface 810 further defines a third region 818. Third region 818 is substantially smaller than first and second regions 812 and 814 in this embodiment. Third region 818 provides increased surface area for bonding components of the catheter to catheter tip 800.

Figure 6:
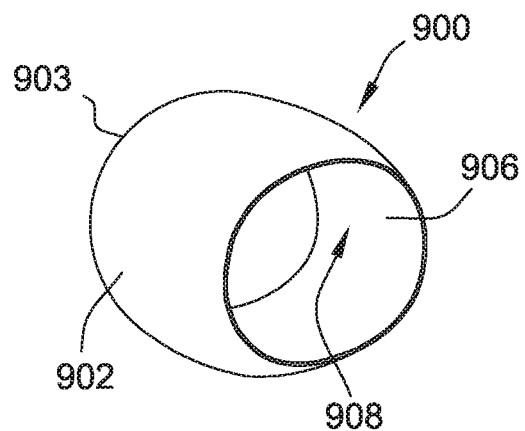
FIG. 6 illustrates an alternative embodiment of a catheter tip in accordance with the present disclosure.

FIG. 6 is a perspective view of another embodiment of a catheter tip 900. An exterior of catheter tip 900 is somewhat similar to that of catheter tip 800. For example, an outer surface 902 of catheter tip 900 narrows to substantially the same diameter as the distal end of catheter shaft 510 at a base 904 of catheter tip 900. In this embodiment, catheter tip 900 has a circular profile at a tip 903 and smoothly transitions to an oval-shaped profile at base 904. This is advantageous in embodiments where the distal end of catheter shaft 510 also has an oval shape. In this embodiment, an interior of the catheter tip 900 does not include a stepped arrangement like catheter tip 800. Instead, an inner surface 906 of catheter tip 900 is smooth and continuous to define a single region 908. In some embodiments, a biocompatible adhesive is applied between inner surface 906 of catheter tip 900 and the distal end of catheter shaft 510 to ensure that catheter tip 900 does not come off during use.

Figures 7A, 7B:
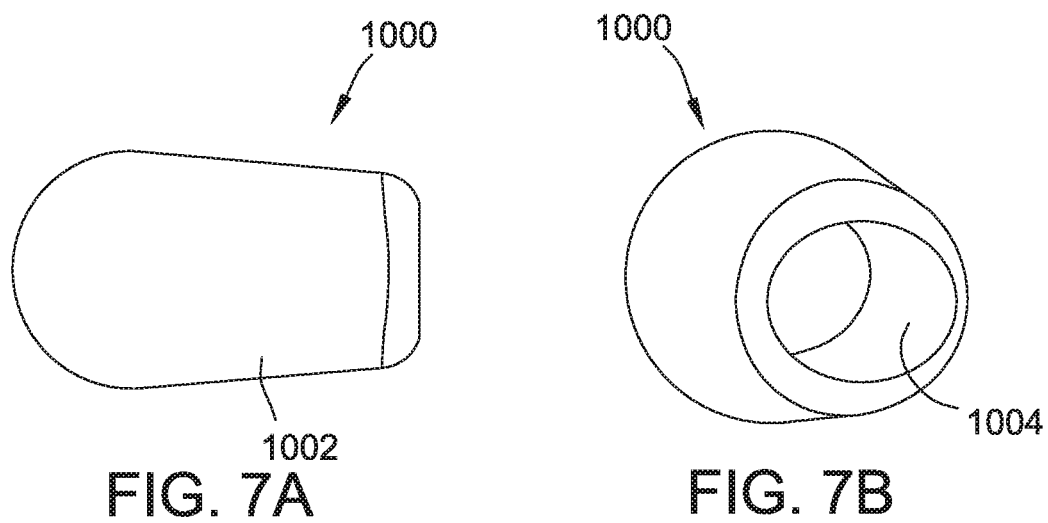
FIGS. 7A and 7B illustrate another alternative embodiment of a catheter tip in accordance with the present disclosure.

FIGS. 7A and 7B illustrate another embodiment of catheter tip 1000. FIG. 7A is a side view of catheter tip 1000, and FIG. 7B is a perspective view of catheter tip 1000. Relative to catheter tips 800 and 900, catheter tip 1000 is more elongated, increasing a surface area for bonding with the distal end of catheter shaft 510. In this embodiment, an outer surface 1002 of catheter tip 1000 has a generally circular profile, and an inner surface 1004 of catheter tip 1000 has a generally oval-shaped profile. Inner surface 1004 of catheter tip 1000 does not include a stepped arrangement as described for catheter tip 800 in FIGS. 5A-5C. In some embodiments, a biocompatible adhesive is used between inner surface 1004 of catheter tip 1000 and the distal end of catheter shaft 510 to ensure that catheter tip 1000 does not come off during use.

Figure 8C:
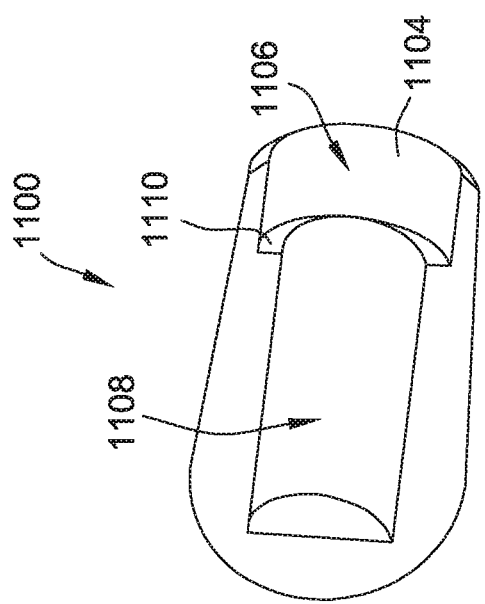
FIGS. 8A-8C illustrate another alternative embodiment of a catheter tip in accordance with the present disclosure.
Figure 8B:
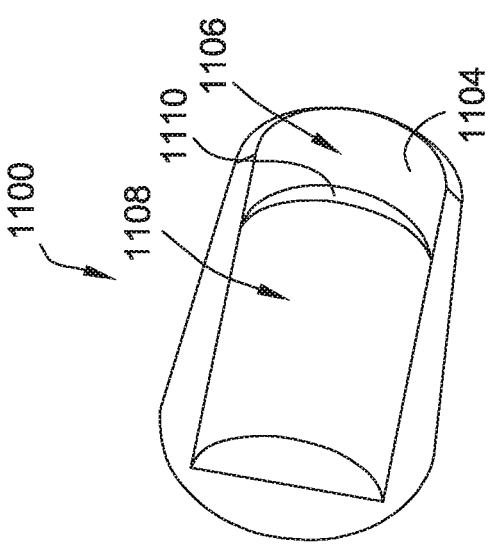
Figure 8A:
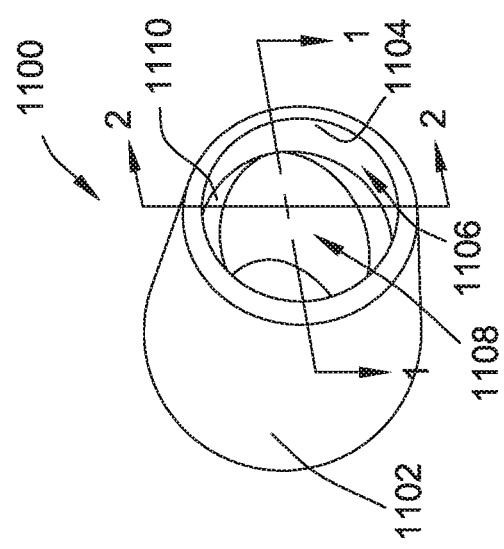

FIGS. 8A-8C illustrate still yet another embodiment of catheter tip 1100. FIG. 8A is a side view of catheter tip 1100, FIG. 8B is a side cross-sectional view of catheter tip 1100 taken along line 1-1, and FIG. 8C is a side cross-sectional view of catheter tip 1100 taken along line 2-2. This embodiment has an outer surface 1002 substantially the same as catheter tip 1000 in FIGS. 7A and 7B. However, an inner surface 1104 of catheter tip 1100 defines a first region 1106 and a second region 1108 distal of first region 1106. Inner surface 1104 has a circular profile in first region 1106 and an oval-shaped profile in second region 1108. Inner surface 1104 defines a lip 1110 between first and second regions 1106 and 1108. In some embodiments, a biocompatible adhesive is used between inner surface 1104 and the distal end of catheter shaft 510 to ensure that catheter tip 1100 does not come off during use.

Figure 9C:
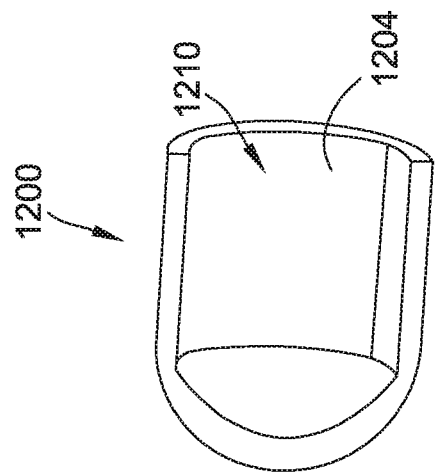
FIGS. 9A-9C illustrate another alternative embodiment of a catheter tip in accordance with the present disclosure.
Figure 9B:
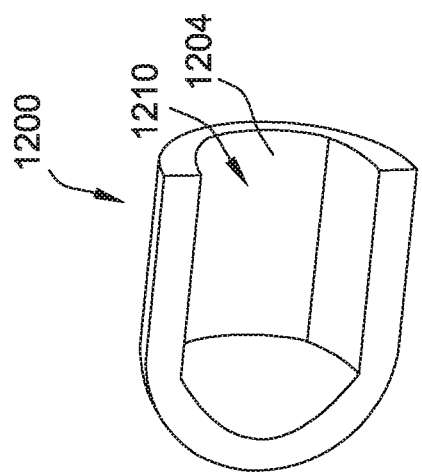
Figure 9A:
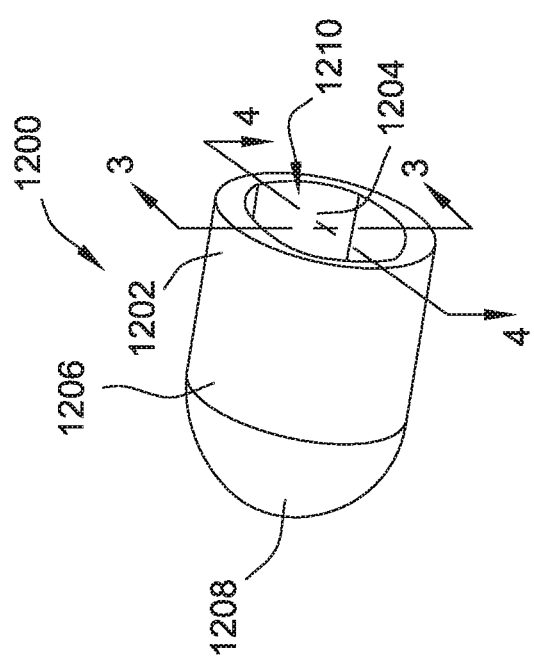

FIGS. 9A-9C illustrate still yet another embodiment of catheter tip 1200. FIG. 9A is a side view of catheter tip 1200, FIG. 9B is a side cross-sectional view of catheter tip 1200 taken along line 3-3, and FIG. 9C is a side cross-sectional view of catheter tip 1200 taken along line 4-4. Catheter tip 1200 includes an outer surface 1202 and an inner surface 1204. Catheter tip 1200 is generally bullet-shaped, with outer surface 1202 forming a cylindrical segment 1206 and a rounded tip 1208. Inner surface 1204 defines a single region 1210, and does not include a stepped arrangement like catheter tip 800. In this embodiment, inner surface 1204 has an oval-shaped profile. In some embodiments, a biocompatible adhesive is used between the inner surface of catheter tip 1200 and the distal end of catheter shaft 510 to ensure that catheter tip 1200 does not come off during use.

Figure 10:
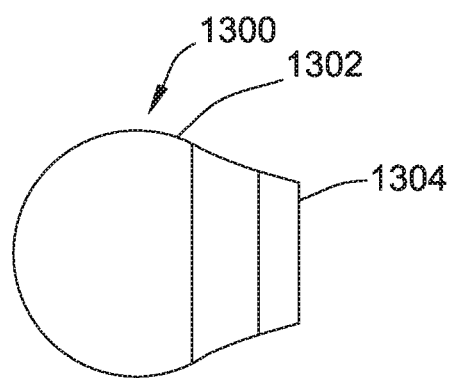
FIG. 10 illustrates another alternative embodiment of a catheter tip in accordance with the present disclosure.

FIG. 10 is a side view of still yet another embodiment of a catheter tip 1300. Catheter tip 1300 has a tapered ball shape where an outer surface 1302 of catheter tip 1300 tapers down to substantially the same size as the diameter of the distal end of catheter shaft 510 at a base 1304 of catheter tip 1300. This embodiment may include a stepped arrangement for inner surface (not shown) as illustrated in FIGS. 5A-5C for catheter tip 800. In some embodiments, a biocompatible adhesive is used between an inner surface (not shown) of catheter tip 1300 and the distal end of catheter shaft 510 to ensure that catheter tip 1300 does not come off during use.

Figure 11:
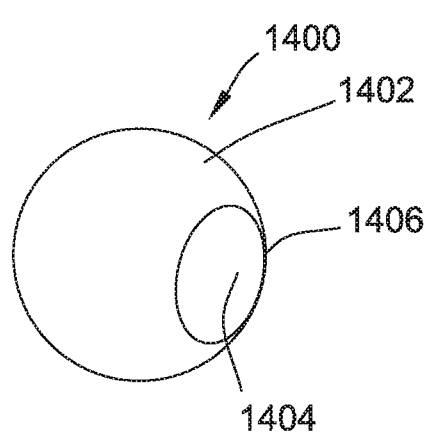
FIG. 11 illustrates another alternative embodiment of a catheter tip in accordance with the present disclosure.

FIG. 11 is a perspective view of still yet embodiment of a catheter tip 1400. Catheter tip 1400 is generally spherical. In catheter tip 1400, an outer surface 1402 tapers to a narrow edge at a base 1406 to create a smooth transition to the distal end of catheter shaft 510. An inner surface 1404 of catheter tip 1400 may optionally have a stepped arrangement as illustrated in FIGS. 5A-5C for catheter tip 800. In some embodiments, a biocompatible adhesive is used between inner surface 1404 of catheter tip 1400 and the distal end of catheter shaft 510 to ensure that catheter tip 1400 does not come off during use.

Figure 12:
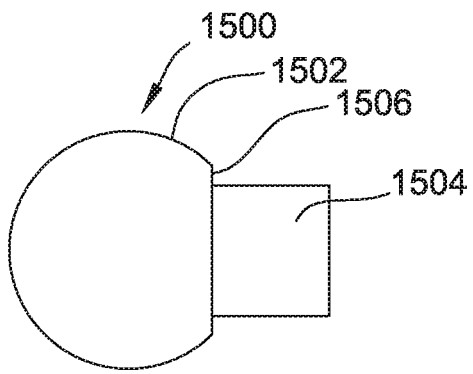
FIG. 12 illustrates another alternative embodiment of a catheter tip in accordance with the present disclosure.

FIG. 12 is a side view of still another embodiment of a catheter tip 1500. This embodiment includes a spherical segment 1502 (similar to catheter tip 1400) and a cylindrical neck 1504 extending from spherical segment 1502. Cylindrical neck 1504 is sized to insert into the distal end of catheter shaft 510. Thus, an outer diameter of neck 1504 is substantially the same as an inner surface diameter of the distal end of catheter shaft 510. The distal end of catheter shaft 510 seats against a lip 1506 formed on spherical segment 1502. In some embodiments, a biocompatible adhesive is used between neck 1504 and the inner surface of the distal end of catheter shaft 510 to ensure that catheter tip 1500 does not come off during use.

Figure 13A:
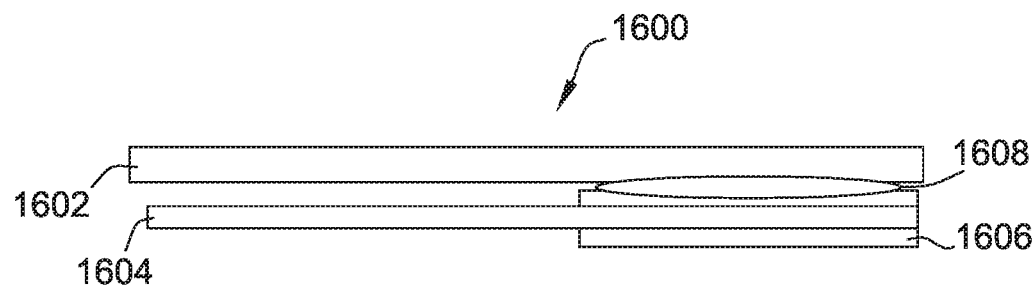
FIGS. 13A-13E illustrate five different stages for a catheter that includes one embodiment of a catheter tip in accordance with the present disclosure.
Figure 13B:
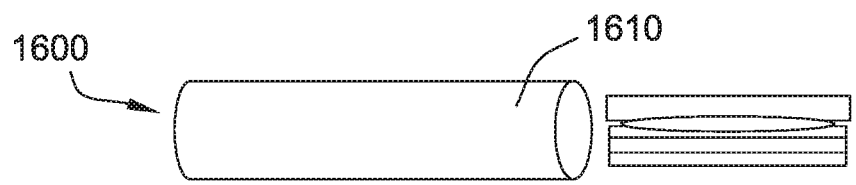
Figure 13C:
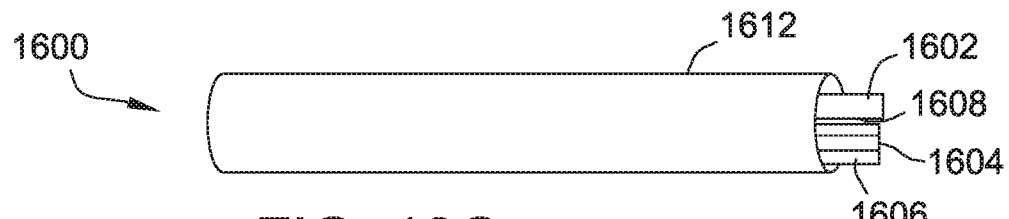
Figure 13D:
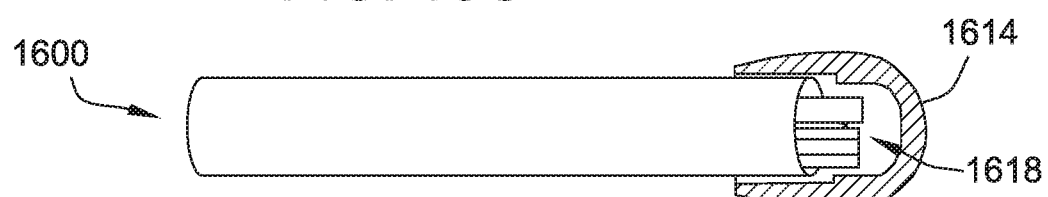
Figure 13E:
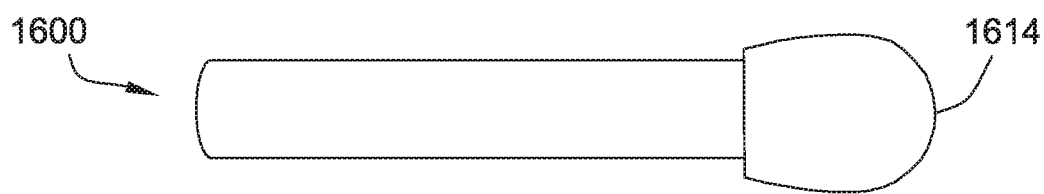

FIGS. 13A-13E illustrate five different stages of a portion of a catheter 1600 that includes one embodiment of a catheter tip 1614 in accordance with the present disclosure. The catheter tip 1614 may be, for example, catheter tip 800 (shown in FIGS. 5A-5C). As shown in FIG. 13A, catheter 1600 includes a pull wire 1604 encompassed in an Inconel sleeve 1606 and a nitinol wire 1602. These components 1602, 1604, and 1606 are held in place relative to one another with a weld-bond 1608. Once bonded, these components 1602, 1604, and 1606 are positioned inside a braided lumen jacket 1610 (as shown in FIG. 13B) which, in turn is encapsulated by a pellethane tube 1612 (As shown in FIG. 13C). Pellethane tube 1612 generally covers most of Inconel sleeve 1606 although, in some aspects, from 0.01 to 0.08 inches of Inconel sleeve 1606 may be exposed. In some aspects, about 0.01 inches, about 0.02 inches, about 0.03 inches, about 0.04 inches, about 0.05 inches, about 0.06 inches, about 0.07 inches or about 0.08 inches of Inconel sleeve 1606 are exposed. The exposed nitinol wire 1602, pull-wire 1604 and Inconel sleeve 1606 are covered with catheter tip 1614. FIG. 13D includes a side cross-sectional view of catheter tip 1614, and FIG. 13D is a side view of catheter tip 1614 and the portion of catheter 1600. As described above, components 1602, 1604, and 1606 extend into at least one region 1618 defined within catheter tip 1614.

Figure 14:
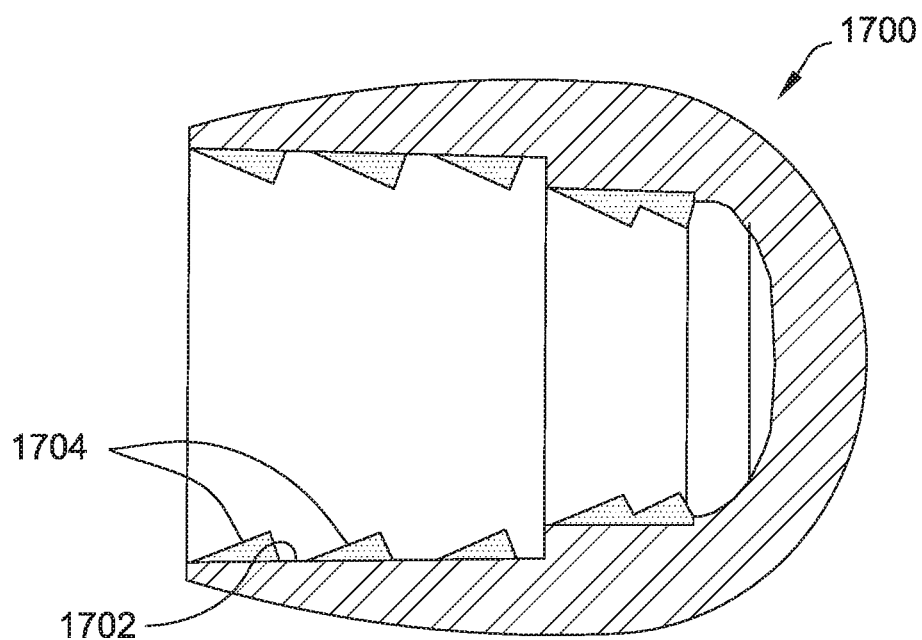
FIG. 14 illustrates another alternative embodiment of the catheter tip in accordance with the present disclosure.

With reference to FIG. 14, there is illustrated yet another embodiment of catheter tip 1700. Catheter tip 1700 is similar to catheter tip 800 (shown in FIGS. 5A-5C). However, catheter tip 1700 includes a plurality of crush tabs 1704 extending from an inner surface 1702. Crush tabs 1704 are sized and configured such that they compress when the distal end of the catheter (not shown in FIG. 17) is inserted into catheter tip 1700. The compressed crush tabs 1704 prevent the distal end of the catheter from inadvertently disengaging from catheter tip 1700. Specifically, crush tabs 1704 exert a pressure against the catheter after insertion, thereby preventing easy removal of catheter tip 1700. Any suitable number of crush tabs 1704 may be utilized in accordance with this embodiment of the present disclosure. Additionally, in further embodiments, catheter tip 1700 may be sized and configured to be screwed or otherwise affixed to the distal end of a catheter shaft.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A catheter tip sized and configured to fit onto a distal end of a catheter shaft, the catheter shaft having a shaft outer diameter, the catheter tip comprising:
    a base;
    a tip having an arcuate shape;
    an outer surface extending from the base to the tip along a longitudinal axis, the outer surface having a diameter at the base that is substantially equal to the shaft outer diameter; and
    an inner surface extending from the base, wherein the inner surface defines a first region having a first diameter and a second region having a second diameter, wherein the second diameter is less than the first diameter, wherein the second region is distal of the first region and configured to receive at least one component extending beyond the distal end of the catheter shaft, wherein the inner surface includes a first portion oriented parallel to the longitudinal axis and defining the first region, a second portion oriented parallel to the longitudinal axis and defining the second region, and a lip extending between the first portion and the second portion, the lip oriented perpendicular to the longitudinal axis, the first portion, and the second portion,
    wherein the inner surface further defines a third region distal of the second region, wherein the third region is smaller than the first and second regions, and wherein the third region terminates in an end wall that is oriented perpendicular to the longitudinal axis.

2. The catheter tip of claim 1, wherein the inner surface is affixed to the distal end of the catheter shaft using an ultraviolet curable adhesive.

3. The catheter tip of claim 1, wherein the catheter tip is formed from a polycarbonate material.

4. The catheter tip of claim 1, wherein the catheter tip further comprises crush tabs extending from the inner surface and configured to prevent removal of the catheter tip from the distal end of the catheter shaft.

5. The catheter tip of claim 1, wherein a cross-sectional profile of the catheter tip along the longitudinal axis is generally circular.

6. A catheter assembly comprising:
    a catheter handle;
    a catheter shaft having a shaft outer diameter, a proximal end, and a distal end; and
    a catheter tip coupled to the distal end of the catheter shaft, the catheter tip comprising:
    a base;
    a tip having an arcuate shape;
    an outer surface extending from the base to the tip along a longitudinal axis, the outer surface having a diameter at the base that is substantially equal to the shaft outer diameter; and
    an inner surface extending from the base, wherein the inner surface defines a first region having a first diameter and a second region having a second diameter, wherein the second diameter is less than the first diameter, wherein the second region is distal of the first region and configured to receive at least one component extending beyond the distal end of the catheter shaft,
    wherein the inner surface includes a first portion oriented parallel to the longitudinal axis and defining the first region, a second portion oriented parallel to the longitudinal axis and defining the second region, and a lip extending between the first portion and the second portion, the lip oriented perpendicular to the longitudinal axis, the first portion, and the second portion,
    wherein the inner surface further defines a third region distal of the second region, wherein the third region is smaller than the first and second regions, and wherein the third region terminates in an end wall that is oriented perpendicular to the longitudinal axis.

7. The catheter assembly of claim 6, wherein the inner surface is affixed to the distal end of the catheter shaft using an ultraviolet curable adhesive.

8. The catheter assembly of claim 6, wherein the catheter tip is formed from a polycarbonate material.

9. The catheter assembly of claim 6, wherein the catheter tip further comprises crush tabs extending from the inner surface and configured to prevent removal of the catheter tip from the distal end of the catheter shaft.

10. The catheter assembly of claim 6, wherein a cross-sectional profile of the catheter tip along the longitudinal axis is generally circular.

* * * * *